United States Patent
Chen et al.

(10) Patent No.: US 8,420,832 B2
(45) Date of Patent: *Apr. 16, 2013

(54) OPTICALLY ACTIVE METHYLHYDROXYLAMINOPROPANOL DERIVATIVE AND ITS USE AS INTERMEDIATE FOR PREPARATION OF (S)-(-)-3-METHYLAMINO-1-(-2-THIENYL)PROPAN-1-OL

(75) Inventors: Bo-Fong Chen, Taoyuan (TW); Jinun-Ban Yeh, Taoyuan (TW); Weichyun Wong, Taoyuan (TW)

(73) Assignee: Sci Pharmtech, Inc., Taoyuan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/436,253

(22) Filed: Mar. 30, 2012

(65) Prior Publication Data

US 2012/0190869 A1    Jul. 26, 2012

Related U.S. Application Data

(60) Division of application No. 12/120,748, filed on May 15, 2008, now Pat. No. 8,168,805, which is a continuation-in-part of application No. 11/926,772, filed on Oct. 29, 2007, now Pat. No. 7,829,731.

(51) Int. Cl.
*C07D 333/12* (2006.01)

(52) U.S. Cl.
USPC .......................................................... 549/75

(58) Field of Classification Search ................ 549/75
See application file for complete search history.

(56) References Cited

U.S. PATENT DOCUMENTS

| 7,259,264 | B2 | 8/2007 | Sturmer |
| 2008/0171887 | A1 | 7/2008 | Pospisilik et al. |
| 2009/0112000 | A1 | 4/2009 | Chen et al. |

FOREIGN PATENT DOCUMENTS

WO    2008077645 A1    7/2008

*Primary Examiner* — Taofiq A Solola
(74) *Attorney, Agent, or Firm* — Sughrue Mion, PLLC

(57) ABSTRACT

The present invention provides an (S)-methylhydroxylaminopropanol compound and the (S)-methylhydroxylaminopropanol compound of the present invention is used as an intermediate for preparation of (S)-(−)-3-methylamino-1-(2-thienyl)propan-1-ol, which is an intermediate for preparation of (S)-(+)-N-methyl-3-methyl-3-(1-naphthyloxy)-3-(2-thienyl)propylamine oxalate. The present invention also provides a process for preparing (S)-(+3-methylamino-1-(2-thienyl)propan-1-ol with higher yield and lower cost, wherein the (S)-methylhydroxylaminopropanol compound is used as an intermediate.

6 Claims, No Drawings

OPTICALLY ACTIVE METHYLHYDROXYLAMINOPROPANOL DERIVATIVE AND ITS USE AS INTERMEDIATE FOR PREPARATION OF (S)-(−)-3-METHYLAMINO-1-(-2-THIENYL)PROPAN-1-OL

CROSS REFERENCE TO RELATED APPLICATION

This is a Divisional of application Ser. No. 12/120,748 filed May 15, 2008, allowed Dec. 27, 2011, which is a continuation in part of application Ser. No. 11/926,772, filed Oct. 29, 2007, now U.S. Pat. No. 7,829,731, the contents of all of which are incorporated herein by reference in their entireties.

BACKGROUND OF THE INVENTION

1. Field of the Invention

The present invention relates to a novel chiral methylhydroxylaminopropanol derivative and its use as an intermediate for preparation of (S)-(−)-3-methylamino-1-(2-thienyl) propan-1-ol.

2. Description of Related Art 3-methylamino-1-(2-thienyl)propan-1-ol, especially its optically active enatiomer (the S form), has been shown to be an important intermediate for preparation of (S)-(+)-N-methyl-3-methyl-3-(1-naphthyloxy)-3-(2-thienyl)propylamine oxalate (Duloxetine®), an antidepressant drug. Various methods have been proposed to prepare (S)-(−)-3-methylamino-1-(2-thienyl)propan-1-ol. For example, *Chirality*, 12, 26 (2000) discloses a process as shown in the following scheme:

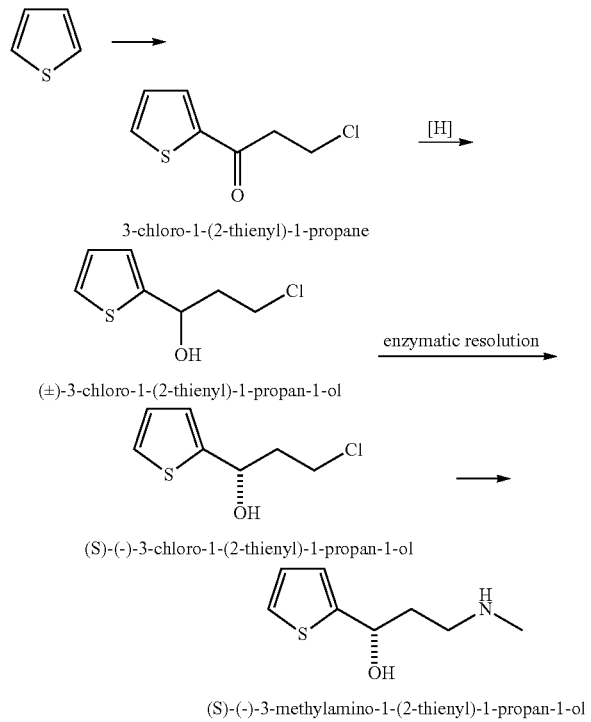

In this example, thiophene is used as the starting material to be acylated by Friedel-Crafts reaction so as to form 3-chloro-1-(2-thienyl)-propanone. Hydride reduction of this propanone forms racemic 3-chloro-1-(2-thienyl)-propan-1-ol. Racemic 3-chloro-1-(2-thienyl)-propan-1-ol is then resolved via enzymatic transesterification to form (S)-(−)-3-chloro-1-(2-thienyl)-propan-1-ol. Subsequently, the resulting chiral chloropropanol is aminated to form (S)-(−)-3-methylamino-1-(2-thienyl)-propan-1-ol with methylamine. In this process, the yield of enzymatic resolution is very low (35%). In addition, large excess, 20 equivalents, of methylamine is required for the amination reaction and the overall yield is low (24%), which renders this process economically less competitive.

SUMMARY OF THE INVENTION

In light of the above-mentioned drawbacks of the prior art, a primary objective of the present invention is to provide a novel (S)-methylhydroxylaminopropanol derivative of formula (II)

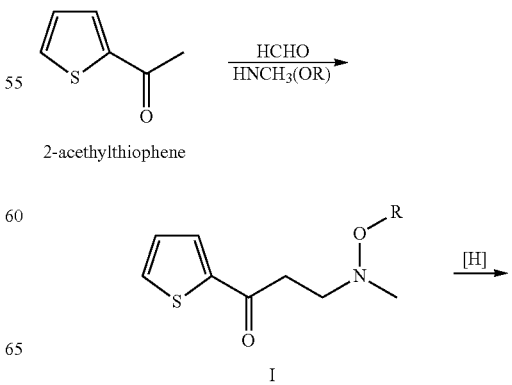

wherein R is a hydrogen atom, an alkyl group having 1 to 8 carbon atoms or an aryl group having 6 to 10 carbon atoms. The absolute configuration of the chiral center is S.

It is another objective of the present invention to provide a process for preparing (S)-(−)-3-methylamino-1-(2-thienyp-propan-1-ol with higher yield and lower cost by using the (S)-methylhydroxylaminopropanol derivative of formula (II) as the intermediate.

To achieve the above-mentioned and other objectives, the process for preparing (S)-(−)-3-methylamino-1-(2-thienyl)-propan-1-ol of the present invention includes steps of: (i) performing a Mannich reaction of 2-acetylthiophene, formaldehyde and a methylhydroxylamine of formula, HNCH$_3$(OR), to form a substituted amino ketone of formula (I); (ii) reducing the substituted amino ketone of formula (I) enatio selectively to form (S)-methylhydroxylaminopropanol derivative of formula (II); and (iii) performing an N, O-cleavage reaction of the (S)-methylhydroxylaminopropanol derivative of formula (II) to form (S)-(−)-3-methylamino-1-(2-thienyl)-propan-1-ol;

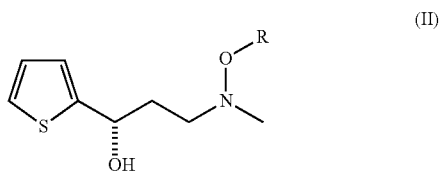

-continued

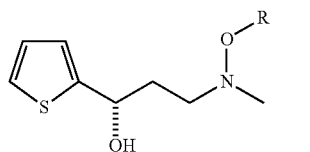

II

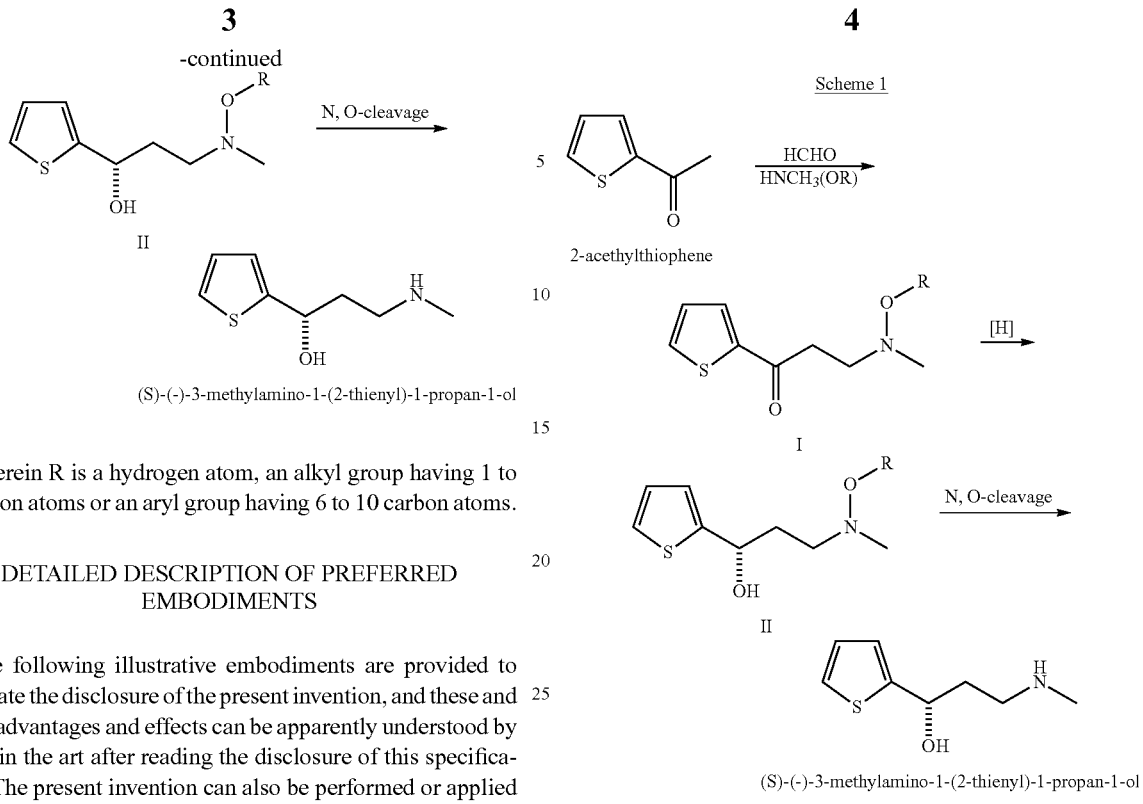

Scheme 1

(S)-(-)-3-methylamino-1-(2-thienyl)-1-propan-1-ol wherein R is a hydrogen atom, an alkyl group having 1 to 8 carbon atoms or an aryl group having 6 to 10 carbon atoms.

DETAILED DESCRIPTION OF PREFERRED EMBODIMENTS

The following illustrative embodiments are provided to illustrate the disclosure of the present invention, and these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

The present invention provides a novel methylhydroxylaminopropanol derivative of formula (II) in optical active form:

(II)

wherein R is a hydrogen atom, an alkyl group having 1 to 8 carbon atoms or an aryl group having 6 to 10 carbon atoms. The absolute configuration of the chiral center is S.

R in the above formula (II) is preferably an alkyl group having 1 to 4 carbon atoms, and is more preferably methyl group.

In addition, the present invention provides the use of (S)-methylhydroxylaminopropanol derivatives of formula (II) as an intermediate for preparation of (S)-(−)-3-methylamino-1-(2-thienyl)propan-1-ol.

It is known that (S)-(−)-3-methylamino-1-(2-thienyppropan-1-ol is an important intermediate for preparation of (S)-(+)-N-methyl-3-methyl-3-(1-naphthyloxy)-3-(2-thienyl) propylamine oxalate (Duloxetine®), which is an antidepressant drug. The process for preparing (S)-(−)-3-methylamino-1-(2-thienyl)-propan-1-ol in the present invention is summarized in Scheme 1.

In Scheme 1, R is a hydrogen atom, an alkyl group having 1 to 8 carbon atoms or an aryl group having 6 to 10 carbon atoms.

In more details, the process of the present invention includes the steps of:
(i) performing a Mannich reaction of 2-acetylthiophene, formaldehyde and a methylhydroxylamine of formula, HNCH₃(OR), to form a substituted amino ketone of formula (I);
(ii) reducing the substituted amino ketone of formula (I) enatio selectively to form (S)-methylhydroxylaminopropanol derivative of formula (II); and
(iii) performing an N, O-cleavage reaction of (S)-methylhydroxylaminopropanol derivative of formula (II) to form (S)-(−)-3-methylamino-1-(2-thienyl)-propan-1-ol.

The step (i) of the process is carried out at a temperature ranged from 90° C. to 15° C., preferably 80° C. to 40° C., and more preferably 70° C. to 50° C. The substituted amino ketone of formula (I) obtained in the step (i) is either as a free form or as an acid addition salt.

The reduction of the substituted amino ketone of formula (I) in the step (ii) is performed by asymmetric reduction, and the optically active form of the (S)-methylhydroxylaminopropanol derivative of formula (II) is obtained. The optically active form can be obtained via asymmetric hydrogenation using catalyst with chiral ligands or hydride with chiral ligands.

In one preferred embodiment, reduction of the substituted amino ketone of formula (I) in the step (ii) is carried out in a mixture of an alcohol such as methanol and base such as potassium tert-butoxide, in the presence of chiral catalyst such as RuCl₂((R)-3,5-xylylBINAP) ((2R)-BMPMBDA). The reaction mixture is hydrogenated at predetermined pressure to yield (S)-methylhydroxylaminopropanol with high ee value.

The N, O-cleavage reaction of the (S)-methylhydroxylaminopropanol derivative of formula (II) in the step (iii) of the process is carried out by hydrogenation in the presence of a catalyst such as Raney-nickel, or by chemical reduction methods such as those using LiAlH$_4$ or zinc metal as reducing agent.

In one preferred embodiment, the methylhydroxylaminopropanol derivative of formula (II) is hydrogenated in methanol in the presence of Raney-nickel at a temperature ranged from 80° C. to 15° C., preferably 70° C. to 40° C., for 9 to 15 hours.

Compared with the conventional process, (S)-(–)-3-methylamino-1-(2-thienyl)-propan-1-ol can be obtained optically pure with higher yield and lower cost from the process of the present invention.

EXAMPLES

Example 1

Synthesis of 3-methoxymethylamino-1-(2-thienyl)-1-propanone hydrochloride salt

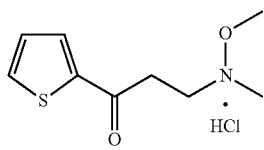

27.7 g of N,O-dimethylhydroxylamine hydrochloride, 9.3 g of paraformaldehyde, 6.4 g of 32% hydrochloride, 30.0 g of 2-acetylthiophene and 100 g of isopropanol were provided into a flask. After being stirred at 60° C. for 13 hours, the reaction mixture was cool down to room temperature. The crystal thus formed was filtered, washed with 30 g of isopropanol and dried under reduced pressure to obtain 42.5 g of 3-methoxymethylamino-1-(2-thienyl)-1-propanone hydrochloride salt (75.9%). $^1$H NMR (400 MHz, CDCl$_3$) δ (ppm)=3.1 (s, 3H), 3.7-3.8 (br, 4H), 4.1 (s, 3H), 7.2 (t, J=4.5 Hz, 1H), 7.7 (d, J=4.9 Hz, 1H), 7.9 (d, J=3.5 Hz, 1H).

Example 2

Synthesis of (S)-3-methoxymethylamino-1-(2-thienyl)propan-1-ol

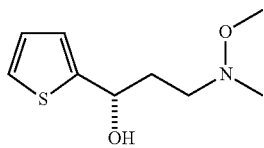

4 mL of degassed methanol solution containing 10 mg of RuCl$_2$((R)-3,5-xylylBINAP) ((2R)-BMMBDA), 160 mg of 3-methoxymethylamino-1-(2-thienyl)-1-propanone, 100 mg of potassium tert-butoxide and 10 mL of methanol were provided in a glass autoclave under an argon gas flow. After deaeration and replacement by argon, hydrogen was introduced to a predetermined pressure. The resulting solution was hydrogenated at 20° C. for 12 hours. Upon completion of hydrogenation, the reaction mixture was concentrated to obtain objective compound as an oily product (161 mg, 95.8% by HPLC assay, 95% ee). $^1$H NMR (400 MHz, CDCl$_3$) δ (ppm)=3.0 (s, 3H), 3.0-3.1 (m, 1H), 4.1 (s, 3H), 4.0-4.1 (m, 3H), 6.1 (dt, J=7.4, 15.4 Hz, 1H), 6.9 (d, J=15.7 Hz, 1H), 7.0 (dd, J=3.7, 5.0 Hz, 1H), 7.1 (d, J=3.4 Hz, 1H).

Example 3

Synthesis of (S)-(–)-3-methylamino-1-(2-thienyl) propan-1-ol

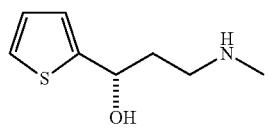

(S)-3-methoxymethylamino-1-(2-thienyl)propan-1-ol obtained in example 2 dissolved in 10 mL of methanol with 8 mg of Raney-nickel were provided in a glass autoclave. The resulting solution was hydrogenated at 50□ for 12 hours. Upon completion of hydrogenation, the reaction mixture was filtered and the solvent was removed under reduced pressure to obtain objective compound as a crystal compound (122 mg, 90.8% by HPLC assay, 95% ee). The crude product was further purified by re-crystallization in toluene with optical purity as high as 100% ee.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. An optical active (S)-methylhydroxylaminopropanol compound of formula (II) or its acid addition salts thereof:

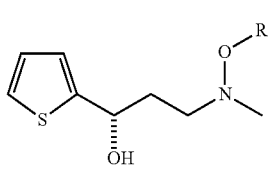

(II)

wherein R is an alkyl group having 1 to 8 carbon atoms or an aryl group having 6 to 10 carbon atoms, and the absolute configuration of the chiral center is S.

2. The (S)-methylhydroxylaminopropanol compound of formula (II) according to claim 1, wherein R is an alkyl group having 1 to 4 carbon atoms.

3. The (S)-methylhydroxylaminopropanol compound of formula (II) according to claim 2, wherein R is methyl group.

4. A process for preparing (S)-methylhydroxylaminopropanol compound of formula (II) according to claim 1, comprising the steps of:

(i) performing a Mannich reaction of 2-acetylthiophene, formaldehyde and a methylhydroxylamine of formula HNCH$_3$(OR), to form a substituted amino ketone of formula (I);

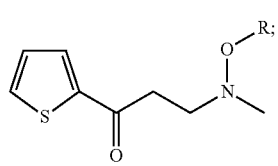
and
(ii) reducing the substituted amino ketone of formula (I) enatio selectively to form (S)-methylhydroxylamino-propanol compound of formula (II).
5. The process according to claim 4, wherein the step (i) is performed at a temperature ranged from 90° C. to 15° C.
6. The process according to claim 4, wherein the step (ii) is performed at pH value ranged from 6 to 14.
* * * * *